United States Patent [19]
Dotolo et al.

[11] Patent Number: 5,346,652
[45] Date of Patent: Sep. 13, 1994

[54] NAIL POLISH REMOVER COMPOSITION

[75] Inventors: Vincent A. Dotolo, Clearwater; John R. Schwartz, Largo; Jaye Kraus-Marchak, Dunedin, all of Fla.

[73] Assignee: Dotolo Research Corporation, Largo, Fla.

[21] Appl. No.: 851,738

[22] Filed: Mar. 16, 1992

[51] Int. Cl.⁵ .................. A61K 7/047; C11D 7/32; C11D 7/26; C11D 7/50
[52] U.S. Cl. ............................. 252/542; 134/38; 252/153; 252/162; 252/171; 252/DIG. 8; 424/61; 424/401
[58] Field of Search ............... 252/542, 153, 162, 170, 252/171, 364, DIG. 8; 424/61, 401; 134/38

[56] References Cited

U.S. PATENT DOCUMENTS

| | | | |
|---|---|---|---|
| 3,686,701 | 8/1972 | Charle et al. | 252/364 |
| 4,533,487 | 8/1985 | Jones | 252/170 |
| 4,620,937 | 11/1986 | Dellutri | 252/143 |
| 4,780,235 | 10/1988 | Jackson | 252/170 |
| 5,063,057 | 11/1991 | Spellman | 424/401 |
| 5,082,660 | 1/1992 | Dunanian et al. | 424/63 |
| 5,098,591 | 3/1992 | Stevens | 252/162 |
| 5,110,584 | 5/1992 | Medri et al. | 424/61 |
| 5,139,570 | 8/1992 | Castrogiovanni et al. | 106/3 |
| 5,145,671 | 9/1992 | Castrogiovanni et al. | 424/61 |
| 5,188,675 | 2/1993 | Dorman-Brailsford | 134/4 |

Primary Examiner—Linda Skaling
Attorney, Agent, or Firm—Marshall & Melhorn

[57] ABSTRACT

A liquid, non-aqueous cleaner composition that is well suited for removing finger nail polish, the composition comprising d-limonene, N-methyl pyrrolidone and cetyl acetate.

15 Claims, No Drawings

NAIL POLISH REMOVER COMPOSITION

FIELD OF THE INVENTION

The present invention relates to a coating removal and all-purpose cleaning composition and, more particularly, to a fingernail polish remover and artificial fingernail tip remover composition.

BACKGROUND OF THE INVENTION

Conventional nail polish remover compositions generally include acetone, ethyl acetate and alcohol. The use of acetone, ethyl acetate and alcohol is disadvantageous in that it gives off a disagreeable odor, is irritating to the eyes and skin, and is drying to the nails and cuticles. Acetone, ethyl acetate and alcohol are flammable and combustible and can be harmful to the user.

OBJECTS OF THE INVENTION

It is an object of the present invention to provide an easy-to-make, easy-to-use very efficient nail polish remover composition or an artificial nail remover composition and methods of using the compositions.

It is a further object of the present invention to provide a very effective, non-toxic, non-methylene chloride, acetone, ethyl acetate or alcohol containing nail polish remover comprising d-limonene, N-methyl-2 pyrrolidone and cetyl acetate.

Still another object of the present invention to provide a non-aqueous liquid cleaning composition especially adapted for removing finger nail polish, the composition comprising the following ingredients in approximate percent by weight:

| Ingredients | % by weight |
| --- | --- |
| 1. d-limonene | 5-75 |
| 2. N-methyl pyrrolidone | 5-95 |
| 3. cetyl acetate | 1-15 |

These and other objects will be apparent from the specification and claims that follow.

SUMMARY OF THE INVENTION

The present invention provides a non-aqueous composition comprising the following ingredients:
1. d-limonene;
2. N-methyl-2 pyrrolidone; and
3. cetyl acetate.

The present invention also provides an effective, non-toxic, non-aqueous liquid finger nail cleaner composition comprising the following ingredients in the general and preferred ranges set forth in approximate percent by weight:

| Ingredients | % by weight General | Preferred |
| --- | --- | --- |
| 1. d-limonene | 5-75 | 40-70 |
| 2. N-methyl pyrrolidone | 5-95 | 25-45 |
| 3. cetyl acetate | 1-15 | 3-10 |

DETAILS OF THE INVENTION

The compositions of the present invention, while preferably used as a nail polish remover, can be used for an artificial nail tip remover, on silk line, and fiberglass wraps. The compositions are useful as all-purpose cleaners and, in particular, hard surface cleaners, blanket washes for us in the printing industry, cleaners for brake linings, silk screens, copier belts, all kinds of metering devices including coin collecting machines, and the cleaning of all types of spraying equipment when used for painting, applying glues, inks, greases, oils, etc.

The easy to use, easy to make cleaning composition is made by mixing the three liquid ingredients (d-limonene, N-methyl pyrrolidone and cetyl acetate) to form a homogenized stable cleaning mixture having enhanced detergent and stripping powers. When generally about one-half to 15% by weight and preferably 8 to 12% by weight of the d-limonene is replaced by ethyl lactate, the speed of the cleaning action increases. This combination is necessary for the removal of some of the new hard finishes of certain nail polishes, especially when the polishes are on wrapped nails. The d-limonene component is a solvent or diluent that assists in penetrating and stripping or removing of the coating (such as finger nail polish) to be removed.

The d-limonene helps to loosen or dissolve grease, fat or organic materials, and is described as an ingredient in a cleaner in U.S. Pat. Nos. 4,790,951 and 5,031,648.

The N-methyl pyrrolidone is a solvent that is compatible with d-limonene and cetyl acetate and the ingredient, preferably N-methyl 2-pyrrolidone (NMP), is listed as a component in compositions in U.S. Pat. Nos. 4,120,810 and 4,732,695. U.S. Pat. No. 4,605,670 discloses a percutaneous (drug) absorption composition including NMP and other ingredients such as alcohols or esters including cetyl acetate. U.S. Pat. No. 5,011,621 is directed to a paint stripper composition and discloses is directed to a paint stripper composition and discloses the use of NMP, an oil, and a plurality of cosolvents including terpenes.

The cetyl acetate is a desensitizer that enhances the compatibility, efficiency, miscibility, and stability of the liquid non-aqueous d-limonene/NMP combination. As indicated, cetyl acetate should be at least about ½ percent by weight of the composition with the best results being obtained with about 4 to 6 percent by weight. In some cases, a small amount of the cetyl acetate, say about ½ to 30 weight percent and preferably about 5 to 10% can be replaced by acetylated lanolin alcohol.

As indicated, small amounts of ethyl lactate can be used as well as small amounts, about ½ to 10% by weight, of an anti-fungicidal agent, myristalkonium chloride and Quaterniun 14 (quaternary ammonium salt derivative) to enhance the cleaner composition and make it more acceptable to the hands. Ethyl lactate is a solvent that is compatible with d-limonene, cetyl acetate, and N-methyl pyrrolidone. Ethyl lactate enhances the compatibility, efficiency, miscibility, and the stability of the liquid, non-aqueous d'limonene/NMP combination and enhances the removal time for the more difficult hard nail polish surfaces. Best results are obtained with about 10% by weight and reducing d-limonene by 10% weight ethyl lactate. As indicated, the total amount of d-limonene in the composition is preferably at least 45 percent by weight and more preferably at least about 50 or 55 percent by weight. In some cases, methyl lactate can be used with the ethyl lactate, the methyl lactate being generally about 3 to 5 weight percent up to 50 to 55 weight percent of the combination of ethyl lactate and methyl lactate.

The cleaner composition has an outstanding balance of properties including easy removal of coatings (finger nail polish) on hard surfaces, being non-irritating, having a pleasant order, being quick drying, having miscible ingredients, and leaving the cleaned surfaces free of surface fiber.

The present invention provides the following compositions:

| Ingredients | A % by weight |
|---|---|
| 1. d-limonene | 55–65 |
| 2. N-methyl pyrrolidone | 30–40 |
| 3. cetyl acetate | 4–6 |

Also provided is a composition comprising about 60 weight percent d-limonene, 35 weight percent N-methyl pyrrolidone, and 5 weight percent cetyl acetate.

Also provided is a composition comprising about 50% by weight of d-limonene, about 25% by weight of N-methyl pyrrolidone, about 5% by weight of cetyl acetate and acetylated lanolin alcohol, about 10% by weight ethyl lactate, and about 10% by weight methyl lactate.

What is claimed is:

1. A fingernail polish remover and a finger artificial nail tip remover non-aqueous composition consisting essentially of the following ingredients:
   a) d-limonene
   b) about 25 to 45 weight percent of N-methyl-2-pyrrolidone
   c) about 1 to 15 weight percent cetyl acetate, the d-limonene being at least 50% by weight of the composition.

2. A non-aqueous cleaning composition consisting essentially of the following ingredients in approximate percent by weight:

| Ingredients | % by weight |
|---|---|
| 1. d-limonene | 40–70 |
| 2. N-methyl pyrrolidone | 25–45 |
| 3. cetyl acetate | 3–10 |

3. A composition as defined in claim 2 in which the following ingredients are present in approximate percent by weight:

| Ingredients | % by weight |
|---|---|
| 1. d-limonene | 55–65 |
| 2. N-methyl pyrrolidone | 30–40 |
| 3. cetyl acetate | 4–6 |

4. A composition as defined in claim 2 consisting essentially of containing about 60 weight percent d-limonene, 35 weight percent N-methyl pyrrolidone, and 5 weight percent cetyl acetate.

5. A composition as defined in claim 2 in which 0.5 to 10 weight percent of the d-limonene is substituted for by an equal weight percent of ethyl lactate.

6. A composition as defined in claim 1 that is effective as a fingernail polish remover and as artificial fingernail tip remover, there being at least about 3 weight percent cetyl acetate.

7. A composition as defined in claim 2 in which the d-limonene is the major component in the composition.

8. A composition as defined in claim 1 in which 0.5 to 10 weight percent of the d-limonene is substituted for by an equal weight percent of ethyl lactate.

9. A composition as defined in claim 1 in which 0.5 to 10 weight percent of the d-limonene is substituted for by an equal weight percent of a mixture of ethyl lactate and methyl lactate wherein said mixture consists of about 3 to 55 weight percent methyl lactate, the balance of said mixture being ethyl lactate.

10. A composition as defined in claim 2 in which 0.5 to 10 weight percent of the d-limonene is substituted for by an equal weight percent of a mixture of ethyl lactate and methyl lactate wherein said mixture consists of about 3 to 55 weight percent methyl lactate, the balance of said mixture being ethyl lactate.

11. A non-aqueous liquid composition consisting essentially of about 50% by weight of d-limonene, about 25% by weight of N-methyl pyrrolidone, about 5% by weight of a mixture of cetyl acetate and acetylated lanolin alcohol wherein said mixture consists of from about 0.5 to 30% by weight of acetylated lanolin alcohol, the balance of said mixture being cetyl acetate, about 10% by weight of ethyl lactate, and about 10% be weight of methyl lactate.

12. A non-aqueous cleaning composition consisting of about 5 to 75% by weight of d-limonene, about 5 to 95% by weight of N-methyl-2-pyrrolidone, and about 1 to 15% by weight of a mixture of cetyl acetate and acetylated lanolin alcohol wherein said mixture consists of from about 0.5 to 30% by weight of acetylated lanolin alcohol, the balance of said mixture being cetyl acetate.

13. A non-aqueous cleaning composition consisting of about 5 to 75% by weight d-limonene, about 5 to 95% by weight of N-methyl-2-pyrrolidone and about 1 to 10% by weight of cetyl acetate.

14. A non-aqueous cleaning composition consisting of the following ingredients in approximate percent by weight:

| Ingredient | % by weight |
|---|---|
| d-limonene | 40–70 |
| N-methyl-2-pyrrolidone | 25–45 |
| mixture of cetyl acetate and acetylated lanolin alcohol | 3–10 |

15. A method of removing a coating from a fingernail comprising:
   a) applying the cleaning composition defined in claim 1 or claim 2 to the coating on the nail;
   b) allowing the coated nail and composition to remain in contact for a time sufficient to loosen the coating from the nail, and
   c) separating the coating and the composition from the nail.

* * * * *